United States Patent
Subotski et al.

(10) Patent No.: US 10,197,636 B1
(45) Date of Patent: Feb. 5, 2019

(54) EXTENDED FAULT INDICATION AND REPORTING IN VOLTAGE REGULATOR SYSTEMS

(71) Applicant: Infineon Technologies Austria AG, Villach (AT)

(72) Inventors: Aliaksandr Subotski, Villach (AT); Giuseppe Bernacchia, Villach (AT); Danny Clavette, Greene, RI (US); Benjamim Tang, Rancho Palos Verdes, CA (US)

(73) Assignee: Infineon Technologies Austria AG, Villach (AT)

( * ) Notice: Subject to any disclaimer, the term of this patent is extended or adjusted under 35 U.S.C. 154(b) by 16 days.

(21) Appl. No.: 15/647,048

(22) Filed: Jul. 11, 2017

(51) Int. Cl.
| | |
|---|---|
| *G01R 31/40* | (2014.01) |
| *H02M 3/156* | (2006.01) |
| *H02M 1/08* | (2006.01) |
| *H02H 7/12* | (2006.01) |
| *G01N 25/72* | (2006.01) |
| *H02M 1/00* | (2006.01) |

(52) U.S. Cl.
 CPC ............. *G01R 31/40* (2013.01); *G01N 25/72* (2013.01); *H02H 7/1213* (2013.01); *H02M 1/08* (2013.01); *H02M 3/156* (2013.01); *H02M 2001/0032* (2013.01)

(58) Field of Classification Search
 None
 See application file for complete search history.

(56) References Cited

U.S. PATENT DOCUMENTS

| | | | |
|---|---|---|---|
| 9,543,838 B2 | 1/2017 | Babazadeh et al. | |
| 9,570,979 B2 | 2/2017 | Tang et al. | |
| 2011/0051479 A1* | 3/2011 | Breen et al. | H02M 3/1584 363/148 |
| 2015/0303799 A1* | 10/2015 | Tang et al. | H02M 3/158 323/271 |
| 2016/0154037 A1 | 6/2016 | Kasturi et al. | |

OTHER PUBLICATIONS

"High-Performance DrBLADE", Infineon Technologies AG, TDA21320, Data Sheet, Revision 2.4, Jul. 16, 2015.

* cited by examiner

*Primary Examiner* — Clayton E Laballe
*Assistant Examiner* — Jas Sanghera
(74) *Attorney, Agent, or Firm* — Murphy, Bilak & Homiller, PLLC (57) ABSTRACT

A voltage regulator controller includes a first pin for receiving aggregate temperature information from a plurality of power stages, a plurality of second pins each for receiving phase current information from one of the power stages, control circuitry for controlling the power stages, detection circuitry for detecting signal levels at the first and second pins, and fault analysis circuitry for identifying the type of reported fault and the power stage that reported the fault based on the detected signal levels at the first and second pins and state information accessible by the controller. Aggregate temperature information is reported at the first pin in a first nominal range, and phase current information is reported at each of the second pins in a second nominal range. Each reported fault type has a unique fault signature at the first and second pins, which is outside at least one of the nominal ranges.

26 Claims, 4 Drawing Sheets

|  | IMON high fault range (2.4 - 3.3V) | IMON nom range (1.0-2.0 V) | IMON low fault range (0 - 0.6V) |
|---|---|---|---|
| TMON low fault range (0 - 0.2 V) | BOOT UVLO | VDD UVLO | VDD UVLO |
| TMON nom range (0.4 - 2.0 V) | OCP POS | NOM | OCP NEG |
| TMON high fault range (2.4 - 3.3 V) | HBS |  | OTP |

EXTENDED FAULT INDICATION AND REPORTING IN VOLTAGE REGULATOR SYSTEMS

TECHNICAL FIELD

The present application relates to voltage regulators, in particular power stage fault indication and reporting.

BACKGROUND

Integrated power stages, used in voltage regulators, have various monitoring and protection features. When a protection event (fault) occurs in a power stage, the power stage should be identified/flagged to the controller which reacts accordingly to ensure safe operation of the entire voltage regulator system. A reported fault indicates a critical condition with high stress levels on the power stage and/or load that require immediate action to prevent imminent catastrophic failure. For example, after fault detection, the controller can set the output of the faulty power stage to tri-state and so that the output voltage is discharged by the load. In another approach, the controller permanently turns on the low-side power transistor of the faulty power stage to prevent destruction of the load. In yet another approach, the controller continues operation until a more severe condition is detected.

Typical protection features implemented in an integrated power stage include: Over Temperature Protection (OTP); Over Current Protection (OCP); High Side Short/Control power transistor Short Detection (HSS); and BOOT voltage under voltage lockout (BOOT UVLO). The BOOT UVLO fault condition indicates that the high-side power transistor of a power stage is being driven with an insufficiently low voltage. Fault conditions are typically reported from an individual power stage to the controller by requiring each power stage to signal a fault condition at a dedicated pin (widely referred to as TMON or TMON/FAULT). This pin is often used to report power stage temperature information when no faults are detected. In the event of a fault, the fault is reported over the dedicated pin using out-of-band signalling i.e. by using signal levels outside of the nominal range used to report temperature information over the pin. In a simplified design, the dedicated pin (TMON or TMON/FAULT) from all power stages are connected to the same signal line (e.g. by a wired-OR connection), and this common connection is coupled to a corresponding dedicated pin of the controller. This simplified implementation is widely adopted in multiphase voltage regulator system, were each power stage provides one phase (current) of the system. With this simplification, the controller cannot distinguish among faults reported by different power stages. As such, the controller cannot identify which power stage is communicating a fault. As a consequence, the controller typically either ignores the fault or shuts down the entire system.

SUMMARY

According to an embodiment of a power stage for a voltage regulator, the power stage comprises one or more power transistor switches configured to output a phase current for the power stage, one or more power transistor gate drivers configured to turn the one or more power transistor switches off and on, and fault detection circuitry configured to detect one or more faults in the power stage, including: positive and negative overcurrent faults in which the phase current exceeds a positive or negative current limit; an overtemperature fault in which the temperature of the power stage exceeds a temperature limit; a phase fault in the power transistor output stage; a boot supply under-voltage fault in which a voltage of a boot capacitor coupled to the one or more power transistor gate drivers is below a target boot voltage level; and a supply under-voltage fault in which a supply voltage of the power stage is below a target supply voltage level. The power stage further comprises reporting circuitry configured to monitor and report information of the power stage, including: report temperature information for the power stage in a first nominal range at a first pin of the power stage when no faults are detected, report phase current information for the power stage in a second nominal range at a second pin of the power stage when no faults are detected, report any of the faults in an out-of-band range outside the first nominal range at the first pin and/or in an out-of-band range outside the second nominal range at the second pin, so that each type of fault which the fault detection circuitry is configured to detect has a unique fault signature at the first and the second pins.

According to an embodiment of a controller for a voltage regulator, the controller comprises: a first pin configured to receive aggregate temperature information from a plurality of power stages coupled to the first pin, the aggregate temperature information indicating the highest temperature reported by all of the power stages; a plurality of second pins, each second pin configured to receive phase current information from one of the power stages; control circuitry configured to control operation of the power stages; and detection circuitry configured to detect signal levels at the first and the second pins, wherein the aggregate temperature information is reported to the controller at the first pin in a first nominal range and the phase current information is reported to the controller at each of the second pins in a second nominal range. The controller further comprises fault analysis circuitry configured to identify a type of fault reported to the controller and the power stage that reported the fault based on the detected signal levels at the first and the second pins and further based on state information accessible by the controller, each fault type reported to the controller having a unique fault signature at the first and the second pins which is outside at least one of the first and the second nominal ranges.

According to an embodiment of a voltage regulator system, the system comprises a plurality of power stages and a controller. Each power stage comprises, one or more power transistor switches configured to output a phase current for the power stage, one or more power transistor gate drivers configured to turn the one or more power transistor switches off and on, fault detection circuitry configured to detect one or more faults in the power stage, including: positive and negative overcurrent faults in which the phase current exceeds a positive or negative current limit; an overtemperature fault in which the temperature of the power stage exceeds a temperature limit; a phase fault in the power transistor output stage; a boot supply under-voltage fault in which a voltage of a boot capacitor coupled to the one or more power transistor gate drivers is below a target boot voltage level; and a supply under-voltage fault in which a supply voltage of the power stage is below a target supply voltage level. Each power stage also comprises reporting circuitry configured to monitor and report information of the power stage, including: report temperature information for the power stage in a first nominal range at a first pin of the power stage when no faults are detected; report phase current information for the power stage in a second nominal range at a second pin of the power stage when no faults are detected; and report any of the faults in an out-of-band range outside the first nominal range at the first pin and/or in an out-of-band range outside the second nominal range at the second pin, so that each type of fault which the fault detection circuitry is configured to detect has a unique fault signature at the first and the second pins. The controller comprises: a first pin coupled to the first pin of each power stage and configured to receive aggregate temperature information from the plurality of power stages, the aggregate temperature information indicating the highest temperature reported by all of the power stages; a plurality of second pins, each second pin of the controller coupled to the second pin of one of the power stages and configured to receive phase current information from that power stage; control circuitry configured to control operation of the power stages; detection circuitry configured to detect signal levels at the first and the second pins of the controller, wherein the aggregate temperature information is reported to the controller at the first pin of the controller in a first nominal range and the phase current information is reported to the controller at each of the second pins of the controller in a second nominal range; and fault analysis circuitry configured to identify a type of fault reported to the controller and the power stage that reported the fault based on the detected signal levels at the first and the second pins of the controller and further based on state information accessible by the controller, each fault type reported to the controller having a unique fault signature at the first and the second pins of the controller which is outside at least one of the first and the second nominal ranges.

Those skilled in the art will recognize additional features and advantages upon reading the following detailed description, and upon viewing the accompanying drawings.

BRIEF DESCRIPTION OF THE FIGURES

The elements of the drawings are not necessarily to scale relative to each other. Like reference numerals designate corresponding similar parts. The features of the various illustrated embodiments can be combined unless they exclude each other. Embodiments are depicted in the drawings and are detailed in the description which follows.

DETAILED DESCRIPTION

The embodiments described herein provide expanded fault indication and reporting capability in voltage regulator (VR) systems, by providing the VR controller precise fault signature information which permits the VR controller to identify each affected power stage and corresponding fault type. No change in the interface between the power stages and the VR controller is needed. A unique fault signature can be maintained from every power stage to the VR controller by proper power stage operation under particular fault conditions. Accordingly, the VR controller can be programmed to respond in a more intelligent and timely manner to a detected fault. For example, depending of the severity of the fault, the VR controller can exclude from regulation the power stage reporting the fault without shutting down the entire voltage regulator system. Moreover, by distinguishing and localizing reported faults, the VR controller can track fault occurrences over time. This information can be used to understand whether some faults are caused by the power stages or by a system weakness such as, but not limited to, poor board layout, other components, etc. System design, robustness and reliability are improved with the fault indication approaches described herein.

Figure 1:
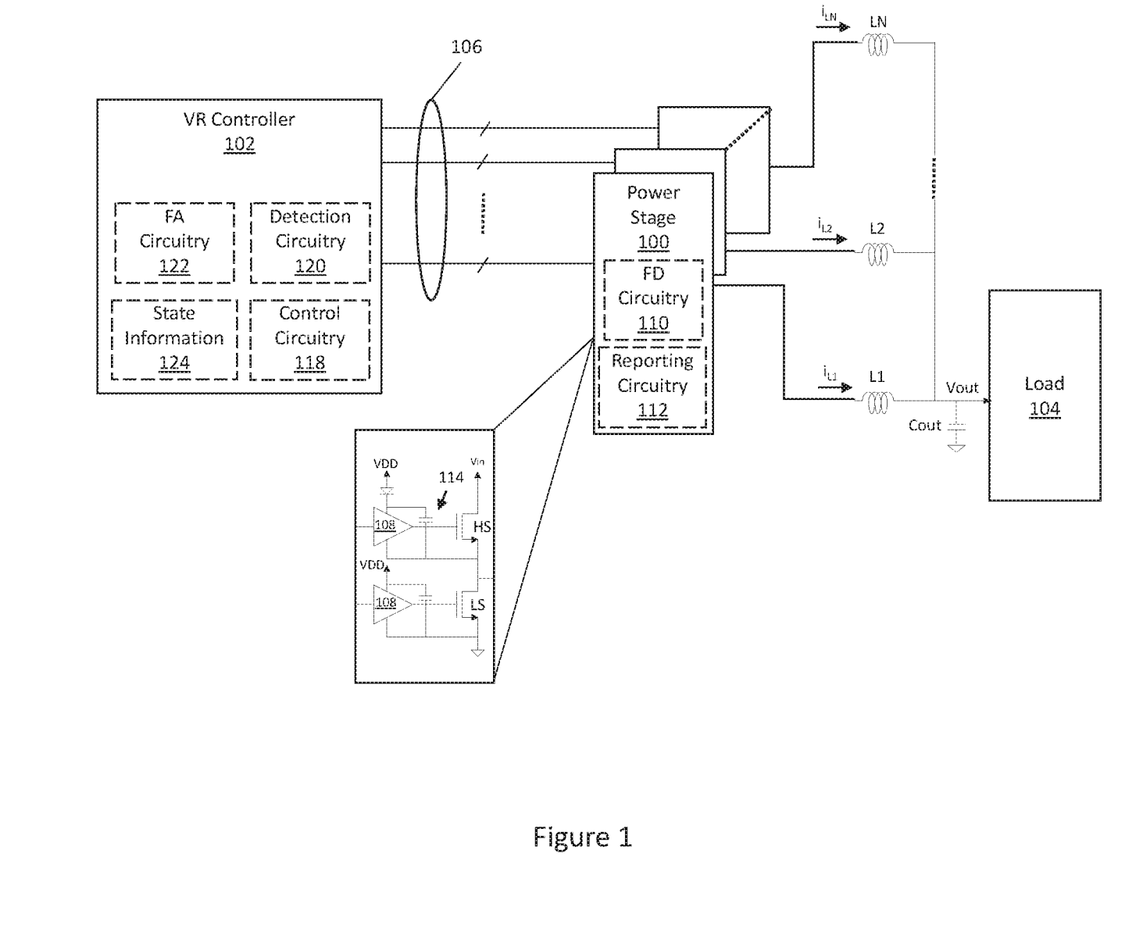
FIG. 1 illustrates a block diagram of an embodiment of a voltage regulator (VR) system with expanded fault indication and reporting capability.

FIG. 1 illustrates an embodiment of a voltage regulator (VR) system. The voltage regulator system includes a plurality of power stages 100 and a VR controller 102 for controlling operation of the individual power stages 100, to regulate the output voltage Vout provided to a load 104. Each power stage 100 can be connected to the load 104 via a respective inductor Lx and via an output capacitor Cout, which can be physically implemented as a single capacitor or a bank of capacitors. The load 104 can be an electronic system requiring one or more regulated voltages, such as a processor, ASIC (application-specific integrated circuit), memory device, etc., or the load 104 can be another converter e.g. in the case of a multi-stage voltage converter system.

A communication interface 106 is provided between the VR controller 102 and the individual power stages 100. Control signalling, telemetry reporting and fault reporting are provided over the communication interface 106, which is depicted simplistically in FIG. 1 for ease of illustration. The VR controller 102 and the power stages 100 each have a plurality of pins for connecting to the communication interface 106, the functionality of relevant ones of the pins being described in more detail later herein.

Each power stage 100 of the voltage regulator system includes one or more power transistor switches HS/LS configured to output a phase current $i_{Lx}$ for that power stage 100, one or more power transistor gate drivers 108 configured to turn the one or more power transistor switches HS/LS off and on, fault detection (FD) circuitry 110 configured to detect one or more faults in the power stage 100, and reporting circuitry 112 configured to monitor and report information of the power stage 100. The fault detection circuitry 110 can include any standard circuitry configured to detect the following faults in a power stage 100 of a voltage regulator positive and negative overcurrent (OCP) faults in which the phase current $i_{Lx}$ exceeds a positive or negative current limit; an overtemperature (OTP) fault in which the temperature of the power stage 100 exceeds a temperature limit; a phase (HSS) fault in the power transistor output stage HS/LS; a boot supply under-voltage (UVLO BOOT) fault in which a voltage of a boot capacitor 114 coupled to the one or more power transistor gate drivers 108 is below a target boot voltage level; and a supply under-voltage (VDD UVLO) fault in which the supply voltage (VDD) of the one or more power transistor gate drivers 108 and/or the power stage input voltage (Vin) is below a target supply voltage level. The boot domain can cause a VDD UVLO fault e.g. either due to issues with the boot capacitor 114 or issues with the circuitry power by the boot voltage. In both cases since, the boot domain supplies the power transistor gate driver 108 for the high-side power transistor switch HS and can result in incorrect operation if functioning improperly.

The reporting circuitry 112 of each power stage 100 is configured to monitor and report at least the following information: temperature information for the power stage 100 in a first nominal range at a first pin of the power stage 100 when no faults are detected; phase current information for the power stage 100 in a second nominal range at a second pin of the power stage 100 when no faults are detected; and any of the faults detected by the fault detection circuitry 110. The reporting circuitry 112 reports the faults in an out-of-band range outside the first nominal range at the first pin and/or in an out-of-band range outside the second nominal range at the second pin, so that each type of fault which the fault detection circuitry 110 is configured to detect has a unique fault signature at the first and second pins.

Figure 2:
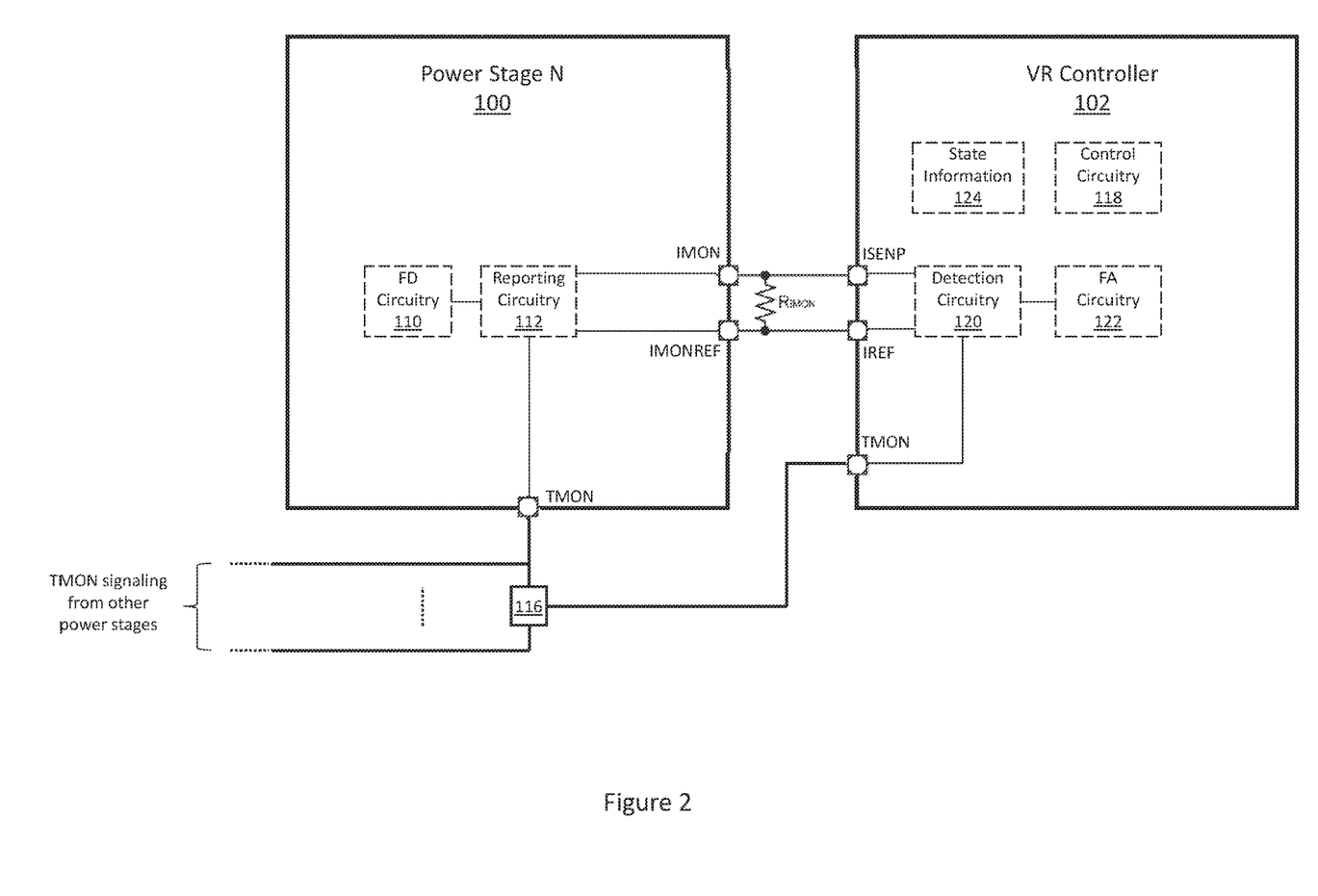
FIG. 2 illustrates a schematic diagram of an embodiment of a communication interface between the VR controller and power stage pins involved in the fault detection and reporting.

FIG. 2 illustrates in more detail the part of the communication interface 106 which includes the VR controller and power stage pins involved in the fault detection and reporting techniques described herein. Each power stage 100 has a first dedicated pin TMON for outputting temperature information for the power stage 100 when no faults are detected. The reported temperature information, e.g. analog voltage information, is proportional to the temperature of the power stage 100. The output of the TMON pin for all power stages 100 can be tied together e.g. in a wired-OR circuit 116 to provide a single shared input to a corresponding first (TMON) pin of the VR controller 102. With this configuration, the VR controller 102 receives aggregate temperature information from the power stages 100 at the TMON pin of the controller 102. The aggregate temperature information indicates the highest temperature reported by all of the power stages 100.

The power stages 100 and the VR controller 102 each have a common pin IMONREF which is an input to the power stages 100 generated by the VR controller 102 or controller supply. Each power stage 100 also has a second dedicated pin IMON for outputting current sense information for the power stage 100 to a corresponding dedicated input pin ISENP of the VR controller 102 when no faults are detected. The reported phase current information, e.g. analog voltage information, is related to the phase current output by the power stage 100 and is used by the VR controller 102 to establish the control loop. The VR controller 102 can determine the individual phase currents of the power stages 100 e.g. based on the voltage across resistor $R_{IMON}$ sensed at the respective pairs of ISENP and IREF pins of the VR controller 102 dedicated for each power stage 100. As previously described herein, the reporting circuitry 112 of each power stage 100 monitors and reports information for that power stage 100, and the fault detection circuitry 110 detects the faults identified above in that power stage 100.

The VR controller 102 includes control circuitry 118 including one or more control loops for controlling operation of the power stages 100. Any standard VR control circuitry can be used, such as but not limited to PMW (pulse width modulation) and related circuitry, sense circuitry for analysing telemetry information reported by the power stages 100 and other system information, etc. The VR controller 102 also includes detection circuitry 120 for detecting signal levels at the pins of the VR controller 102, including at the dedicated TMON, ISENP and IREF pins of the VR controller 102. The reporting circuitry 112 of each power stage 100 reports individual temperature information for the power stage 100 in a first nominal range at the dedicated TMON pin of the power stage 100 when no faults are detected. The reporting circuitry 112 of each power stage 100 also reports phase current information for the power stage 100 in a second nominal range at the dedicated pin IMON of the power stage 100 when no faults are detected. The temperature information from the individual power stages 100 is aggregated and reported to the VR controller 102 at the dedicated TMON pin of the VR controller 102 in the first nominal range, and the individual phase current information from the power stages 100 is reported to the VR controller 102 at each corresponding dedicated ISENP and IREF pins of the VR controller 102 in the second nominal range.

If the VR controller 102 receives phase current and temperature information in the respective nominal ranges, the VR controller 102 may presume each power stage 100 is functioning properly. The VR controller 102 uses the temperature and phase current information to control the power stages 100. The VR controller 102 also includes fault analysis (FA) circuitry 122 for identifying each type of fault reported to the VR controller 102 and the power stage 100 that reported the fault, based on the detected signal levels at the dedicated TMON, ISENP and IREF pins of the VR controller 102, and further based on state information 124 accessible by the VR controller 102.

Each fault type reported to the VR controller 102 has a unique fault signature at the dedicated TMON, ISENP and IREF pins of the controller 102 which is outside at least one of the temperature and phase current information nominal reporting ranges. With this approach, VR system robustness and reliability is increased by extending information flow from the power stages 100 to the VR controller 102 without changing the pre-existing communication interface 106. That is, conventional power stages have dedicated TMON, IMON and IMONREF pins for communicating power stage phase current and temperature information, and conventional VR controllers have corresponding dedicated ISENP, IREF and TMON pins for receiving the phase current and temperature information and for enabling phase current sensing. However, unlike most conventional VR systems that report faults only via the TMON pin, the expanded fault indication and reporting techniques described herein allow the VR controller 102 to identify the faulty power stage and specific fault type. This way, the VR controller 102 can exclude from regulation the power stage 100 causing the fault, thereby continuing operation if possible.

Figure 3:
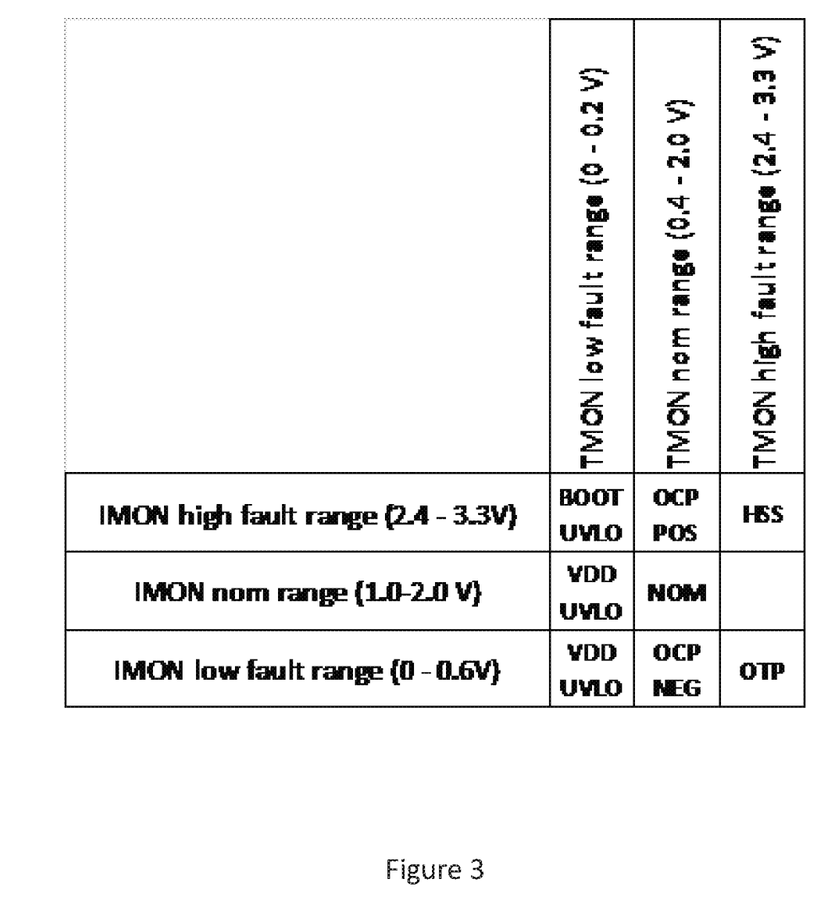
FIG. 3 illustrates an embodiment of the fault signalling implemented between the VR controller and the power stages.

FIG. 3 illustrates an embodiment of the fault signalling implemented by the power stages 100 at the dedicated TMON and IMON pins. In an embodiment, the reporting circuitry 112 of a power stage 100 reports a positive overcurrent (OCP POS) fault in a first signalling band (e.g. 2.4V to 3.3V) outside the nominal range (e.g. 1.0V to 2.0V) used for phase current reporting at the IMON pin. The power stage reporting circuitry 112 also reports a negative overcurrent (OCP NEG) fault in a second signalling band (e.g. 0V to 0.6V) outside the nominal range used for phase current reporting at the IMON pin. The first and second out-of-band signalling ranges are nonoverlapping with each other. A positive overcurrent fault is detected when the phase current $i_{LX}$ output by that power stage 100 exceeds a positive current limit, and the negative overcurrent condition is detected when the phase current $i_{LX}$ output by that power stage 100 exceeds a negative current limit. The power stage fault detection circuitry 114 can include any standard circuitry such as current sense and comparator circuitry for detecting positive and negative overcurrent conditions in a VR power stage.

In an embodiment, the reporting circuitry 112 of each power stage 100 reports a supply under-voltage (VDD UVLO) fault in a signalling band (e.g. 0V to 0.2V) outside the nominal range (e.g. 0.4 V to 2.0 V) used for temperature reporting at the TMON pin. Alternatively or in addition, the power stage reporting circuitry 112 can report the supply under-voltage fault in a first signalling band (e.g. 0V to 0.2V) outside the nominal range (e.g. 0.4 V to 2.0 V) used for temperature reporting at the TMON pin and in a second signalling band (e.g. 0V to 0.6V) outside the nominal range (e.g. 1.0V to 2.0V) used for phase current reporting at the IMON pin. The power stage fault detection circuitry 114 can include any standard circuitry such as a comparator for sensing a low VR supply voltage Vin and/or gate driver supply voltage VDD.

In an embodiment, the reporting circuitry 112 of each power stage 100 reports an overtemperature (OTP) fault in a first signalling band (e.g. 2.4V to 3.3V) outside the nominal range (e.g. 0.4 V to 2.0 V) used for temperature reporting at the TMON pin and in a second signalling band (e.g. 0V to 0.6V) outside the nominal range (e.g. 1.0V to 2.0V) used for phase current reporting at the IMON pin. The power stage fault detection circuitry 114 can include any standard circuitry such as a temperature sensor for sensing an excessive temperature in a VR power stage.

In an embodiment, the reporting circuitry 112 of each power stage 100 reports a phase (HSS) fault in a first signalling band (e.g. 2.4V to 3.3V) outside the nominal range (e.g. 0.4 V to 2.0 V) used for temperature reporting at the TMON pin and in a second signalling band (e.g. 2.4V to 3.3V) outside the nominal range (e.g. 1.0V to 2.0V) used for phase current reporting at the IMON pin. The power stage fault detection circuitry 114 can include any standard circuitry such as a high-side short detector for sensing a phase fault in a VR power stage.

In an embodiment, the reporting circuitry 112 of each power stage 100 reports a boot supply under-voltage (BOOT UVLO) fault in a first signalling band (e.g. 0V to 0.2V) outside the nominal range (e.g. 0.4 V to 2.0 V) used for temperature reporting at the TMON pin and in a second signalling band (e.g. 2.4V to 3.3V) outside the nominal range (e.g. 1.0V to 2.0V) used for phase current reporting at the IMON pin. The power stage fault detection circuitry 114 can include any standard circuitry such as a comparator for sensing an inadequate boot voltage in a VR power stage.

In one embodiment, the reporting circuitry 112 of each power stage 100 reports all of the faults using the out-of-band signalling illustrated in FIG. 3. That is, the power stage reporting circuitry 112: reports the positive overcurrent condition (OCP POS) in a first signalling band (e.g. 2.4V to 3.3V) outside the nominal range (e.g. 1.0V to 2.0V) used for phase current reporting at the IMON pin; reports the negative overcurrent fault (OCP NEG) in a second signalling band (e.g. 0V to 0.6V) outside the nominal range used for phase current reporting at the IMON pin; reports the supply under-voltage fault (VDD UVLO) in a third signalling band (e.g. 0V to 0.2V) outside the nominal range (e.g. 0.4 V to 2.0 V) used for temperature reporting at the TMON pin, or in the third signalling band at the TMON pin and in the second signalling band at the IMON pin; reports the overtemperature fault (OTP) in a fourth signalling band (e.g. 2.4V to 3.3V) outside the nominal range used for temperature reporting at the TMON pin and in the second signalling band at the IMON pin; reports the phase fault (HSS) in the fourth signalling band at the TMON pin and in the first signalling band at the IMON pin; and reports the boot under-voltage fault (BOOT UVLO) in the third signalling band and in the first signalling band at the IMON pin.

The power stage 100 that reports a fault on its TMON pin is not identifiable by the VR controller 102 by the TMON pin signature alone, since the TMON pin is shared by all power stages 100. However, the TMON pin is usable during startup since the TMON signal will enter the nominal range until at least one power stage 100 exits VDD UVLO (supply voltage startup). In the case of OCP POS and OCP NEG faults, both of these faults indicate that the corresponding power stage 100 is truncating PWM pulses, and may be asserted after multiple consecutive cycles that cannot be resolved by current balancing implemented by the VR controller 102. With HSS and OTP faults, the VR controller 102 detects its TMON pin going high and can determine which power stage 100 reported an overtemperature condition and whether an HSS or OTP fault has occurred. The BOOT UVLO and OCP POS faults are initially non-differentiable based on the out-of-band signalling scheme shown in FIG. 3. However, the OCP POS fault will clear after the power stage 100 that reported the OCP POS fault enters sleep mode. The BOOT UVLO fault is not cleared in sleep mode.

A power stage 100 may enter sleep mode after control signals of the one or more power transistor gate drivers 108 indicate that the one or more power transistor switches HS/LS of that power stage 100 should be off for a minimum time period, the gate driver control signals being derived from the corresponding PWM signals from the VR controller 102. In another embodiment, a power stage 100 may enter sleep mode responsive to the level of an input pin separate from the dedicated TMON, IMON and IMONREF pins. In general, the reporting circuitry 112 of each power stage 100 may clear reporting of some faults and not clear reporting of other faults when the power stage 100 enters a non-switching, low power sleep mode. The power stage 100 exits the sleep mode when the control signals indicate that at least one of the one or more power transistor switches HS/LS should be turned on.

The fault out-of-band signalling relations and/or band ranges illustrated in FIG. 3 for fault indication and reporting on the power stage side can be defined differently, while yielding the same result.

On the controller side, the TMON pin output of each power stage 100 can be tied together e.g. by a wired-OR circuit 116 to provide a single shared input to the VR controller 102 for general fault reporting. Individual current sense signals are provided from each power stage 100 via pins IMON and IMONREF from every power stage 100 to respective pairs of dedicated pins INSEP/IREF of the VR controller 102.

Figure 4:
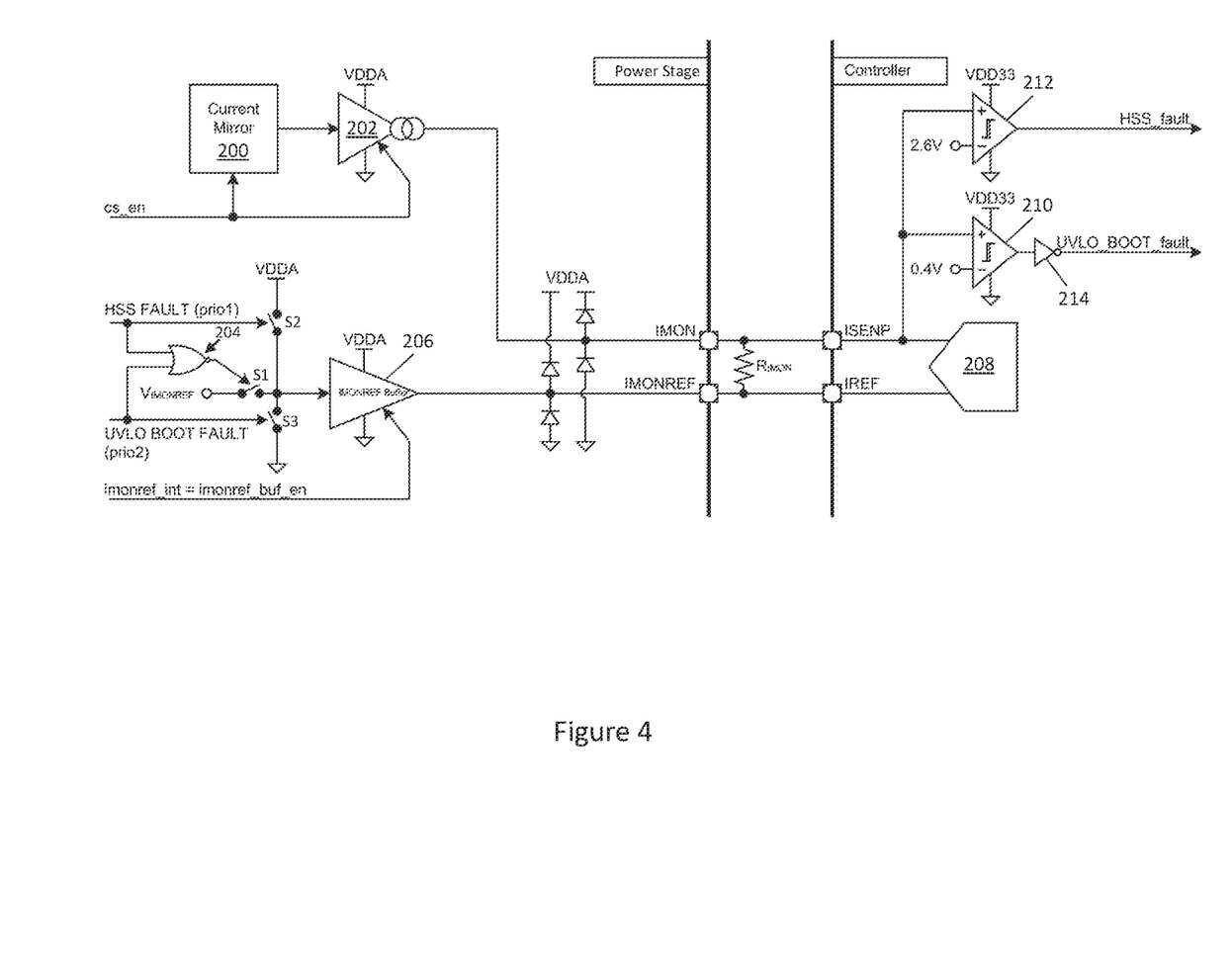
FIG. 4 illustrates a schematic diagram of an embodiment of the power stage to controller interface for supporting recognition of different fault signatures at the VR controller.

FIG. 4 illustrates an embodiment of the power stage to controller interface 106 for supporting recognition of some fault signatures at the VR controller 102. Each power stage 100 includes a current mirror 200 connected to a current reporting circuitry 202 powered by supply voltage VDDA, for generating a signal representative of the phase current $i_{Lx}$ output by that power stage 100. Signal cs_en enables the current reporting circuitry 202 connected to the current mirror 200, so that the phase current signal output from the current mirror 200 is reported in a nominal range at the IMON pin. The IMON and IMONREF pins may be tied via an optional resistor $R_{IMON}$ for current-to-voltage conversion. In the case a power stage 100 reports the voltage at the IMON pin, the optional resistor $R_{IMON}$ is not used. In the case a power stage 100 reports the current at the IMON pin, the optional resistor $R_{IMON}$ is used for current-to-voltage conversion. In this case, if phase current signal is not present, the IMON and IMONREF pins have equal potentials due to resistor $R_{IMON}$.

The reporting circuitry 112 of the power stage 100 manipulates the signal levels at the IMONREF and/or IMON pins to indicate different fault conditions. In one embodiment, the power stage reporting circuitry 112 includes circuitry such as a NOR gate 204, switches S1-S3 and a buffer 206 powered by supply voltage VDDA for providing out-of-band fault signaling at the IMON and IMONREF pins. If no fault has occurred, the IMONREF pin is connected to the default voltage level $V_{IMONREF}$ via the NOR logic gate 204 and a corresponding switch S1 of the power stage reporting circuitry 112. Voltage level $V_{IMONREF}$ is used as a reference level for reporting the phase current information from the current mirror 200 in a nominal signal range. When the fault detection circuitry 114 of the power stage 100 detects the occurrence of an HSS (high-side short-circuit) fault or UVLO BOOT (low boot voltage) fault, the NOR logic gate 204 of the power stage reporting circuitry 112 deactivates the switch S1 connected to $V_{IMONREF}$. In the event of an HSS fault, a corresponding switch S2 of the power stage reporting circuitry 112 is activated. Switch S2 connects the IMONREF pin to voltage VDDA, which is at a voltage level out-of-band from the nominal signal range ($V_{IMONREF}$) used to report the phase current information when no faults are detected. In the event of a UVLO BOOT fault, a corresponding switch S3 of the power stage reporting circuitry 112 is activated. Switch S3 connects the IMONREF pin to ground, which also is at a voltage level out-of-band from the nominal signal range ($V_{IMONREF}$) used to report the phase current information when no faults are detected.

The combination of signalling via the TMON, IMON and IMONREF pins of the power stage 100, as well as power stage state information 124 accessible to the VR controller 102, yields unique fault signatures for the VR controller 102 to detect, which aids the VR controller 102 in recognizing the affected power stage individually and the corresponding fault type. Table 1 provides another embodiment of unique fault signatures detectable at the VR controller 102 by the controller fault analysis circuitry 122, based on the detected signal levels at the TMON, IMON and IMONREF pins of the VR controller 102, and further based on power stage state information 124 accessible by the VR controller 102.

The OTP (overtemperature) fault has a unique signature for the VR controller 102. In the embodiment illustrated in Table 1, the TMON pin of the power stage 100 with the OTP fault is pulled to a high voltage level outside the nominal reporting range for temperature information, but is not latched. During the OTP fault, the power stage 100 ignores the VR controller 102 and stops PWM switching. The power stage 100 also stops phase current reporting at the IMON pin, and keeps the IMON and IMONREF pins at an intermediate voltage level within the nominal reporting range for phase current information (e.g. IMON=IMONREF=1.32V). Entering sleep mode does not clear the OTP fault, but the OTP fault can be cleared by power cycling the affected power stage 100 (powering down the power stage and then powering up again). Based on the out-of-band fault signalling reported at the TMON, equal voltage level within nominal reporting range at the IMON and IMONREF pins and the state information listed in Table 1 for the power stage 100 with the OTP fault and which is available to the VR controller 102, the VR controller 102 can identify the power stage 100 with the OTP fault.

OCP (overcurrent) fault also has a unique signature for the VR controller 102. In the embodiment illustrated in Table 1, the TMON pin for the power stage 100 with the OCP fault is pulled to a high voltage level outside the nominal reporting range for temperature information, but is not latched. The affected power stage 100 continues switching during the OCP fault, unless the VR controller 102 determines otherwise. Accordingly, the PWM signal to the power stage 100 with the OCP fault continues uninterrupted, but perhaps truncated. The power stage 100 continues phase current reporting at the IMON pin during the OCP fault, and entering sleep mode clears the OCP fault. Based on the out-of-band fault signalling reported at the TMON pin and the state information listed in Table 1 for the power stage 100 with the OCP fault and which is available to the VR controller 102, the VR controller 102 can identify the power stage 100 with the OCP fault.

The HSS (high-side short-circuit) fault also has a unique signature for the VR controller 102. In the embodiment illustrated in Table 1, the TMON pin for the power stage 100 with the HSS fault is pulled to a high voltage level outside the nominal reporting range for temperature information,

TABLE 1

| | Signature for Controller | | | | | |
|---|---|---|---|---|---|---|
| Fault Type | Switching | PWM | TMON pin | IMON reporting | Fault cleared by Sleep Mode | Fault cleared by power cycling |
| OTP | no, PWM ignored | Controller is ignored | Pulled High, not latched | no (ΔVIMON = 0; IMON = IMONREF = 1.32 V) | no | yes |
| OCP | yes, no hole in PWM train, just truncation | Controller controls | Pulled High, not latched | yes | yes | yes |
| HSS | yes, allows controller to decide if low-side switch is turned on | Controller controls | Pulled High, latched | no (IMON = IMONREF = "High", latched) (ΔVIMON = 0; IMON = IMONREF > 2.6 V) | no | yes |
| BOOT UVLO | yes, allows controller to decide if low-side switch is turned on | Controller controls | Pulled High, latched | no (IMON = IMONREF = "Low", latched) (ΔVIMON = 0; IMON = IMONREF < 0.4 V) | no | yes | and latched. The affected power stage 100 may continue switching during the HSS fault, e.g. if the VR controller 102 determines that the low-side switch LS of the power-stage 100 should be turned on. The affected power stage 100 also stops phase current reporting at the IMON pin, and latches the IMON and IMONREF pins at a high voltage level outside the nominal reporting range for phase current information (e.g. IMON=IMONREF=>2.6V). Entering sleep mode does not clear the HSS fault, but the HSS fault can be cleared by power cycling the power stage 100. Based on the out-of-band fault signalling reported at the TMON, IMON and IMONREF pins and the state information listed in Table 1 for the power stage 100 with the HSS fault and which is available to the VR controller 102, the VR controller 102 can identify the power stage 100 with the HSS fault.

The UVLO BOOT (low boot voltage) fault also has a unique signature for the VR controller 102. In the embodiment illustrated in Table 1, the TMON pin for the power stage 100 with the UVLO BOOT fault is pulled to a high voltage level outside the nominal reporting range for temperature information, and latched. The affected power stage 100 may continue switching during the UVLO BOOT fault, e.g. if the VR controller 102 determines that the low-side switch LS of the power-stage 100 should be turned on. The affected power stage 100 also stops phase current reporting at the IMON pin, and latches the IMON and IMONREF pins at a low voltage level outside the nominal reporting range for phase current information (e.g. IMON=IMONREF=<0.4V). Entering sleep mode does not clear the UVLO BOOT fault, but the UVLO BOOT fault can be cleared by power cycling the power stage 100. Based on the out-of-band fault signalling reported at the TMON, IMON and IMONREF pins and the state information listed in Table 1 for the power stage 100 with the UVLO BOOT fault and which is available to the VR controller 102, the VR controller 102 can identify the power stage 100 with the UVLO BOOT fault.

The detection circuitry 120 of the VR controller can include ADC (analog-to-digital conversion) circuitry 208 for detecting the signal levels at each pair of ISENP and IREF pins of the VR controller 102 for each power stage 100. The fault analysis circuitry 122 of the VR controller 102 can include comparators 210, 212 and related circuitry 214 for identify a HSS or UVLO BOOT fault type reported to the VR controller 102 and the power stage 100 that reported the fault, based on the detected signal levels at the corresponding ISENP and IREF pins of the VR controller, and further based on the power stage state information accessible by the VR controller 102, e.g. as shown in Table 1.

The control circuitry 118 of the VR controller 102 can report the type of fault and the power stage 100 that reported the fault to a higher-level system associated with the voltage regulator system. The control circuitry 118 of the VR controller 102 can also track power stage faults and corresponding fault types over time, to identify predominant failure mechanisms. In one embodiment, the control circuitry 118 of the VR controller 102 tracks the state of the TMON, ISENP and IREF pins over time to determine whether a power stage fault was cleared when the power stage 100 that reported the fault entered sleep mode, and to determine the corresponding fault type based on the tracked state of the TMON, ISENP and IREF pins.

In general, the state information used by the fault analysis circuitry 122 of the VR controller 102 to identify a fault type and the power stage 100 that reported the fault type can include at least one of information indicating whether the power stage 100 is in start-up mode, information indicating whether the power stage 100 is in a low power mode such as sleep mode, information indicating whether the fault type is cleared by the power stage 100 entering and exiting a low power mode, and information indicating whether the power stage 100 is switching.

Terms such as "first", "second", and the like, are used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

It is to be understood that the features of the various embodiments described herein may be combined with each other, unless specifically noted otherwise.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A power stage for a voltage regulator, the power stage comprising:
   one or more power transistor switches configured to output a phase current for the power stage;
   one or more power transistor gate drivers configured to turn the one or more power transistor switches off and on;
   fault detection circuitry configured to detect one or more faults in the power stage, including:
      positive and/or negative overcurrent faults in which the phase current exceeds a positive or negative current limit;
      an overtemperature fault in which the temperature of the power stage exceeds a temperature limit;
      a phase fault in the power transistor output stage;
      a boot supply under-voltage fault in which a voltage of a boot capacitor coupled to the one or more power transistor gate drivers is below a target boot voltage level; and
      a supply under-voltage fault in which a supply voltage of the power stage is below a target supply voltage level; and
   reporting circuitry configured to monitor and report information of the power stage, including:
      report temperature information for the power stage in a first nominal range at a first pin of the power stage when no faults are detected,
      report phase current information for the power stage in a second nominal range at a second pin of the power stage when no faults are detected,
      report any of the faults in an out-of-band range outside the first nominal range at the first pin and/or in an out-of-band range outside the second nominal range at the second pin, so that each type of fault which the fault detection circuitry is configured to detect has a unique fault signature at the first and the second pins.

2. The power stage of claim 1, wherein the reporting circuitry is configured to report the positive overcurrent fault in a first signalling band outside the second nominal range at the second pin and report the negative overcurrent fault in a second signalling band outside the second nominal range at the second pin, and wherein the first and the second signalling bands are nonoverlapping with each other.

3. The power stage of claim 1, wherein the reporting circuitry is configured to report the supply under-voltage fault in a signalling band outside the first nominal range at the first pin.

4. The power stage of claim 1, wherein the reporting circuitry is configured to report the supply under-voltage fault in a first signalling band outside the first nominal range at the first pin and in a second signalling band outside the second nominal range at the second pin.

5. The power stage of claim 1, wherein the reporting circuitry is configured to report the overtemperature fault in a first signalling band outside the first nominal range at the first pin and in a second signalling band outside the second nominal range at the second pin.

6. The power stage of claim 1, wherein the reporting circuitry is configured to report the phase fault in a first signalling band outside the first nominal range at the first pin and in a second signalling band outside the second nominal range at the second pin.

7. The power stage of claim 1, wherein the reporting circuitry is configured to report the boot supply under-voltage fault in a first signalling band outside the first nominal range at the first pin and in a second signalling band outside the second nominal range at the second pin.

8. The power stage of claim 1, wherein the reporting circuitry is configured to:
report the positive overcurrent fault in a first signalling band outside the second nominal range at the second pin;
report the negative overcurrent fault in a second signalling band outside the second nominal range at the second pin, the first and the second signalling bands being nonoverlapping with each other;
report the supply under-voltage fault in a third signalling band outside the first nominal range at the first pin, or in the third signalling band at the first pin and in the second signalling band at the second pin;
report the overtemperature fault in a fourth signalling band outside the first nominal range at the first pin and in the second signalling band at the second pin, the third and the fourth signalling bands being nonoverlapping with each other;
report the phase fault in the fourth signalling band at the first pin and in the first signalling band at the second pin; and
report the boot supply under-voltage fault in the third signalling band at the first pin and in the first signalling band at the second pin.

9. The power stage of claim 1, where the reporting circuitry is configured to clear reporting of some of the faults and not clear reporting of other ones of the faults when the power stage enters a non-switching, low power sleep mode.

10. The power stage of claim 9, wherein the power stage is configured to enter the sleep mode after control signals of the one or more power transistor gate drivers indicate that the one or more power transistor switches should be off for a minimum time period, and wherein the power stage is configured to exit the sleep mode when the control signals indicate that at least one of the one or more power transistor switches should be turned on.

11. The power stage of claim 9, wherein the power stage is configured to enter the sleep mode responsive to the level of an input pin separate from the first and the second pins.

12. A controller for a voltage regulator, the controller comprising:
a first pin configured to receive aggregate temperature information from a plurality of power stages coupled to the first pin, the aggregate temperature information indicating the highest temperature reported by all of the power stages;
a plurality of second pins, each second pin configured to receive phase current information from one of the power stages;
control circuitry configured to control operation of the power stages;
detection circuitry configured to detect signal levels at the first and the second pins, wherein the aggregate temperature information is reported to the controller at the first pin in a first nominal range and the phase current information is reported to the controller at each of the second pins in a second nominal range; and
fault analysis circuitry configured to identify a type of fault reported to the controller and the power stage that reported the fault based on the detected signal levels at the first and the second pins and further based on state information accessible by the controller, each fault type reported to the controller having a unique fault signature at the first and the second pins which is outside at least one of the first and the second nominal ranges.

13. The controller of claim 12, wherein the fault analysis circuitry is configured to detect positive and/or negative overcurrent faults in which the phase current of a power stage exceeds a positive or negative current limit, an overtemperature fault in which the temperature of a power stage exceeds a temperature limit, a phase fault at a power stage, a boot supply under-voltage fault in which a voltage of a boot capacitor of a power stage is below a target boot voltage level, and a supply under-voltage fault in which a supply voltage of a power stage is below a target supply voltage level.

14. The controller of claim 13, wherein the fault analysis circuitry is configured to detect the positive overcurrent fault based on the detected signal levels at the second pin being in a first signalling band outside the second nominal range and detect the negative overcurrent fault based on the detected signal levels at the second pin being in a second signalling band outside the second nominal range, and wherein the first and the second signalling bands are non-overlapping with each other.

15. The controller of claim 13, wherein the fault analysis circuitry is configured to detect the supply under-voltage fault based on the detected signal levels at the first pin being in a signalling band outside the first nominal range the first pin.

16. The controller of claim 13, wherein the fault analysis circuitry is configured to detect the supply under-voltage fault based on the detected signal levels at the first pin being in a first signalling band outside the first nominal range and the detected signal levels at the second pin being in a second signalling band outside the second nominal range.

17. The controller of claim 13, wherein the fault analysis circuitry is configured to detect the overtemperature fault based on the detected signal levels at the first pin being in a first signalling band outside the first nominal range and the detected signal levels at the second pin being in a second signalling band outside the second nominal range.

18. The controller of claim 13, wherein the fault analysis circuitry is configured to detect the phase fault based on the detected signal levels at the first pin being in a first signalling band outside the first nominal range and the detected signal levels at the second pin being in a second signalling band outside the second nominal range.

19. The controller of claim 13, wherein the fault analysis circuitry is configured to detect the boot supply under-voltage fault based on the detected signal levels at the first pin being in a first signalling band outside the first nominal range and the detected signal levels at the second pin being in a second signalling band outside the second nominal range.

20. The controller of claim 13, wherein the fault analysis circuitry is configured to:
detect the positive overcurrent fault based on the detected signal levels at the second pin being in a first signalling band outside the second nominal range,
detect the negative overcurrent fault based on the detected signal levels at the second pin being in a second signalling band outside the second nominal range, the first and the second signalling bands being nonoverlapping with each other;
detect the supply under-voltage fault based on the detected signal levels at the first pin being in a third signalling band outside the first nominal range, or based on the detected signal levels at the first pin being in the third signalling band and the detected signal levels at the second pin being in the second signalling band;
detect the overtemperature fault based on the detected signal levels at the first pin being in a fourth signalling band outside the first nominal range and the detected signal levels at the second pin being in the second signalling band, the third and the fourth signalling bands being nonoverlapping with each other;
detect the phase fault based on the detected signal levels at the first pin being in the fourth signalling band and the detected signal levels at the second pin being in the first signalling band; and
detect the boot supply under-voltage fault based on the detected signal levels at the first pin being in the third signalling band and the detected signal levels at the second pin being in the first signalling band.

21. The controller of claim 12, wherein the control circuitry is configured to exclude from regulation a power stage that reported a fault to the controller.

22. The controller of claim 12, wherein the control circuitry is configured to report the type of fault and the power stage that reported the fault to a higher-level system associated with the voltage regulator.

23. The controller of claim 12, wherein the control circuitry is configured to track power stage faults and corresponding fault types over time.

24. The controller of claim 12, wherein the state information used by the fault analysis circuitry to identify a fault type and the power stage that reported the fault type comprises at least one of information indicating whether the power stage is in startup mode, information indicating whether the power stage is in a low power mode, information indicating whether the fault type is cleared by the power stage entering and exiting a low power mode, and information indicating whether the power stage is switching.

25. The controller of claim 12, wherein the control circuitry is configured to track the state of the first and the plurality of second pins over time to determine whether a power stage fault was cleared when the power stage that reported the fault entered sleep mode, and determine the corresponding fault type based on the tracked state of the first and the plurality of second pins.

26. A voltage regulator system, comprising:
a plurality of power stages, each power stage comprising:
one or more power transistor switches configured to output a phase current for the power stage;
one or more power transistor gate drivers configured to turn the one or more power transistor switches off and on;
fault detection circuitry configured to detect one or more faults in the power stage, including:
positive and/o negative overcurrent faults in which the phase current exceeds a positive or negative current limit;
an overtemperature fault in which the temperature of the power stage exceeds a temperature limit;
a phase fault in the power transistor output stage;
a boot supply under-voltage fault in which a voltage of a boot capacitor coupled to the one or more power transistor gate drivers is below a target boot voltage level; and
a supply under-voltage fault in which a supply voltage of the power stage is below a target supply voltage level; and
reporting circuitry configured to monitor and report information of the power stage, including:
report temperature information for the power stage in a first nominal range at a first pin of the power stage when no faults are detected;
report phase current information for the power stage in a second nominal range at a second pin of the power stage when no faults are detected; and
report any of the faults in an out-of-band range outside the first nominal range at the first pin and/or in an out-of-band range outside the second nominal range at the second pin, so that each type of fault which the fault detection circuitry is configured to detect has a unique fault signature at the first and the second pins;
a controller comprising:
a first pin coupled to the first pin of each power stage and configured to receive aggregate temperature information from the plurality of power stages, the aggregate temperature information indicating the highest temperature reported by all of the power stages;
a plurality of second pins, each second pin of the controller coupled to the second pin of one of the power stages and configured to receive phase current information from that power stage;
control circuitry configured to control operation of the power stages;
detection circuitry configured to detect signal levels at the first and the second pins of the controller, wherein the aggregate temperature information is reported to the controller at the first pin of the controller in a first nominal range and the phase current information is reported to the controller at each of the second pins of the controller in a second nominal range; and
fault analysis circuitry configured to identify a type of fault reported to the controller and the power stage that reported the fault based on the detected signal levels at the first and the second pins of the controller and further based on state information accessible by the controller, each fault type reported to the controller having a unique fault signature at the first and the second pins of the controller which is outside at least one of the first and the second nominal ranges.

\* \* \* \* \*

UNITED STATES PATENT AND TRADEMARK OFFICE
CERTIFICATE OF CORRECTION

| | |
|---|---|
| PATENT NO. | : 10,197,636 B1 |
| APPLICATION NO. | : 15/647048 |
| DATED | : February 5, 2019 |
| INVENTOR(S) | : A. Subotski et al. |

Page 1 of 1

It is certified that error appears in the above-identified patent and that said Letters Patent is hereby corrected as shown below:

In the Claims

Column 14, Line 54 (Claim 15, Line 4), please change "range the" to -- range of the --.

Column 16, Line 13 (Claim 26, Line 10), please change "and/o" to -- and/or --.

Signed and Sealed this
Ninth Day of April, 2019

Andrei Iancu
*Director of the United States Patent and Trademark Office*